May 24, 1966 W. ZOMBORY ETAL Plant Pat. 2,632
DIANTHUS PLANT
Filed April 20, 1965
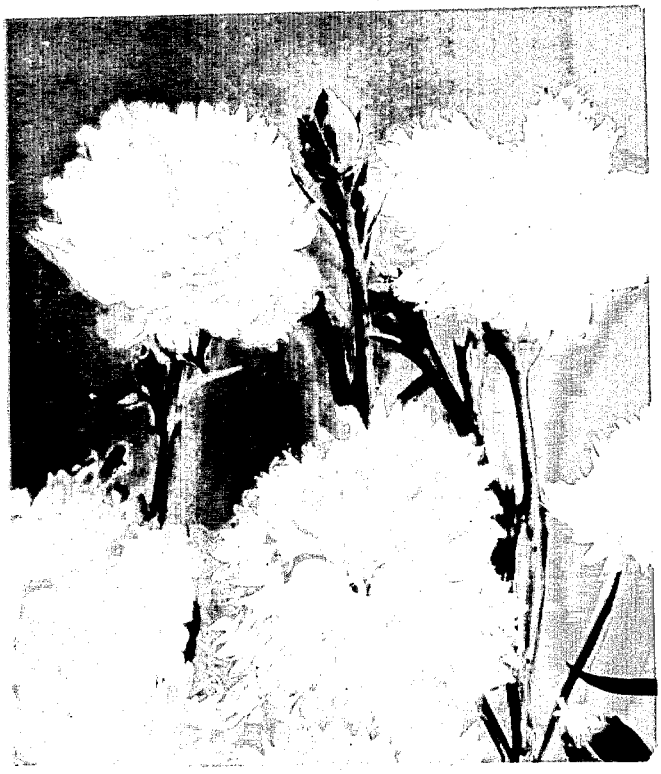
Inventors.
William Zombory and
Sophia B. Zombory
By: Robb & Robb
Attorneys.

United States Patent Office

Plant Pat. 2,632
Patented May 24, 1966

2,632
DIANTHUS PLANT

William Zombory and Sophia B. Zombory, both of Detroit, Mich., assignors to Jackson & Perkins Company, Newark, N.Y., a corporation of New York Filed Apr. 20, 1965, Ser. No. 449,663
1 Claim. (Cl. Plt.—71)

The present invention relates to a new and distinct variety of dianthus plant, which was originated by us by crossing an unnamed and unpatented large white-flowered variety of the species botanically known as "Dianthus allwoodi" with an unnamed and unpatented white flowered seedling of "Dianthus Caprice" (Plant Patent No. 1,851).

The primary objective of this breeding was to produce a new and improved dianthus variety of a more hardy strain and which bears larger and more hardy flowers than those of the parent varieties. This objective was fully achieved along with other desirable improvements as evidenced by the following unique combination of characteristics which are outstanding in our new variety and which distinguish it from its parents, as well as from all other varieties of which we are aware:

(1) An upright and compact habit of growth;

(2) Production of blooms commencing the first year when grown from cuttings;

(3) A continuous blooming habit throughout the season;

(4) A distinctive flower form attributed to lacy edges of the petals;

(5) A distinctive and attractive general color tonality of the flowers corresponding to La France Pink; and (6) A spicy flower fragrance.

Asexual reproduction of our new variety by cuttings, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—An unnamed large white-flowered variety of the species botanically known as "Dianthus allwoodi."

*Pollen parent.*—An unnamed white seedling of "Dianthus Caprice."

Blooming season: Starts blooming the first year when grown from cuttings, with blooms continuing from June until frost.

*Plant*

Growth: Medium tall (about 12 inches); compact.

Leaves: Many bottom leaves in tufts; from 4 inches to 4½ inches long; thick; narrow. Color—Chromium Green, Plate 32, with a silvery sheen of Greenish Glaucous, Plate 41.

Flower stem: About 10 inches long; strong. Color—Light Elm Green, Plate 17.

*Flower*

Borne: From 6 to 10 buds and flowers per stem; borne mostly on own branched stalks, but some of the laterals nearly sessile.

Size: About 2 inches in diameter, but flowers on laterals about 1¼ inches in diameter.

Petals: From 25 to 30 petals; about ¾ inch in width at the widest point; about 1 inch long; with lacy edges. Color: Upper side—La France Pink, Plate 1; reverse side—Hermosa Pink, Plate 1, very lightly overcast with Thulite Pink, Plate 26; claw—White, Plate 53 blended with Glass Green, Plate 31.

Calyx: Cylindrical; teeth about ½ inch long; erect; calyx splits on wide open flowers. Color—teeth Cress Green, Plate 31, with lower half of calyx lightly overcast with Garnet Brown, Plate 1.

Bracts: 4 in number; medium size. Color—Cress Green, Plate 31.

Stamens: 5 or 6 in number; some protruding. Color—White, Plate 53.

Anthers: Color—Pale Lavender-Violet, Plate 25.

Ovary: Small; oval.

Fragrance: Strong. Nature—spicy.

We claim:

A new and distinct variety of dianthus plant, substantially as herein shown and described, characterized particularly as to novelty by the unique combination of an upright and compact habit of growth, production of blooms commencing the first year when grown from cuttings, a continuous blooming habit throughout the season, a distinctive flower form attributed to lacy edges of the petals, a distinctive and attractive general color tonality of the flowers corresponding to La France Pink, and a spicy flower fragrance.

No references cited.

ABRAHAM G. STONE, *Primary Examiner.*